US006780193B2

(12) United States Patent
Leslie et al.

(10) Patent No.: US 6,780,193 B2
(45) Date of Patent: Aug. 24, 2004

(54) SURGICAL EXTRACTOR

(75) Inventors: Stephen W. Leslie, Lorain, OH (US); James S. Bates, Bloomington, IN (US)

(73) Assignee: Boston Scientific Corporation, Natick, MA (US)

( * ) Notice: Subject to any disclaimer, the term of this patent is extended or adjusted under 35 U.S.C. 154(b) by 192 days.

(21) Appl. No.: 10/105,985

(22) Filed: Mar. 25, 2002

(65) Prior Publication Data

US 2002/0151928 A1 Oct. 17, 2002

Related U.S. Application Data

(63) Continuation of application No. 09/636,213, filed on Aug. 10, 2000, now Pat. No. 6,383,196, which is a continuation of application No. 08/968,906, filed on Nov. 6, 1997, now Pat. No. 6,168,603, which is a continuation of application No. 08/822,207, filed on Mar. 20, 1997, now abandoned, which is a continuation of application No. 08/382,778, filed on Feb. 2, 1995, now abandoned.

(51) Int. Cl.[7] .............................................. A61B 17/24
(52) U.S. Cl. ........................ 606/114; 606/127; 606/200
(53) Field of Search ................................ 606/113, 114, 606/127, 200

(56) References Cited

U.S. PATENT DOCUMENTS

| | | | |
|---|---|---|---|
| 1,677,671 A | 7/1928 | Councill |
| 2,556,783 A | 6/1951 | Wallace |
| 2,943,626 A | 7/1960 | Dormia |
| 3,008,467 A | 11/1961 | Morris |
| 3,108,593 A | 10/1963 | Glassman |
| 3,137,298 A | 6/1964 | Glassman |
| 3,472,230 A | 10/1969 | Fogarty |
| 3,791,387 A | 2/1974 | Itoh |
| 4,046,150 A | 9/1977 | Schwartz et al. |
| 4,198,960 A | 4/1980 | Utsugi |

(List continued on next page.)

FOREIGN PATENT DOCUMENTS

| | | |
|---|---|---|
| DE | 4025799 | 2/1992 |
| FR | 2 275 187 | 1/1976 |
| JP | 5-330875 | 8/1978 |
| JP | 3-205043 | 9/1991 |

(List continued on next page.)

OTHER PUBLICATIONS

Phan et al., "Ureteric Retrieval Net: Comparison with Stone Extraction by Dormia Baskets in an In Vitro Porcine Model," *Brit.J. Urol.* 73:33–36, 1994.

*Primary Examiner*—Kevin T. Truong
(74) *Attorney, Agent, or Firm*—Finnegan, Henderson, Farabow, Garrett & Dunner, L.L.P.

(57) ABSTRACT

A surgical extractor for removing objects from a body including, for example, calculi, such as kidney stones and gall stones. The extractor includes a handle at an proximal end of the extractor with a slider for operation by a physician. At the distal end the extractor includes a plurality of wires with each wire comprising a first portion having an individual strand and a second portion comprising a plurality of filaments. When a retaining sheath is retracted, the wires, formed of a shape memory material such as stainless steel, expand such that each of strands assume a spaced relationship to define a first section of a basket and the plurality of the filaments assume a spaced relationship to define a second section of the basket. The use of a basket formed by wires having a first section comprising an individual strand and a second section comprising the plurality of filaments promotes capture of objects within the body by having widely spaced wires in the first section, retention of such objects in the second section by multiplying the number of contacts with entrapped object, and improved selective release of such objects without any deleterious effect on the reliability or size of the extractor. Additionally, use of the basket enables improved dislodgment and capture of embedded or impacted objects.

14 Claims, 5 Drawing Sheets

U.S. PATENT DOCUMENTS

| | | |
|---|---|---|
| 4,299,225 A | 11/1981 | Glassman |
| 4,347,846 A | 9/1982 | Dormia |
| 4,557,255 A | 12/1985 | Goodman |
| 4,590,938 A | 5/1986 | Segura et al. |
| 4,611,594 A | 9/1986 | Grayhack et al. |
| 4,612,931 A | 9/1986 | Dormia |
| 4,625,726 A | 12/1986 | Duthoy |
| 4,633,871 A | 1/1987 | Shinzuka |
| 4,655,219 A | 4/1987 | Petruzzi |
| 4,741,335 A | 5/1988 | Okada |
| 4,790,812 A | 12/1988 | Hawkins, Jr. et al. |
| 4,807,626 A | 2/1989 | McGirr |
| 4,927,426 A | 5/1990 | Dretler |
| 4,997,435 A | 3/1991 | Demeter |
| 5,030,201 A | 7/1991 | Palestrant |
| 5,057,114 A | 10/1991 | Wittich et al. |
| 5,064,428 A | 11/1991 | Cope et al. |
| 5,074,867 A | 12/1991 | Wilk |
| 5,147,371 A | 9/1992 | Washington et al. |
| 5,176,688 A | 1/1993 | Narayan et al. |
| 5,190,542 A | 3/1993 | Nakao et al. |
| 5,190,557 A | 3/1993 | Borodulin et al. |
| 5,192,286 A | 3/1993 | Phan et al. |
| 5,201,740 A | 4/1993 | Nakao et al. |
| 5,496,330 A | 3/1996 | Bates et al. |
| 5,520,697 A | 5/1996 | Lindenberg et al. |
| 5,549,626 A | 8/1996 | Miller et al. |
| 5,658,296 A | 8/1997 | Bates et al. |
| 5,667,525 A | 9/1997 | Ishibashi, deceased |
| 5,755,790 A | 5/1998 | Chevillon et al. |
| 5,836,968 A | 11/1998 | Simon et al. |
| 6,093,196 A * | 7/2000 | Okada .................. 606/127 |

FOREIGN PATENT DOCUMENTS

| | | |
|---|---|---|
| RU | 2022528 | 11/1994 |
| SU | 1036325 | 8/1983 |
| WO | WO92/05828 | 4/1992 |
| WO | WO92/16153 | 10/1992 |
| WO | WO95/05129 | 2/1995 |
| WO | WO96/01591 | 1/1996 |

* cited by examiner

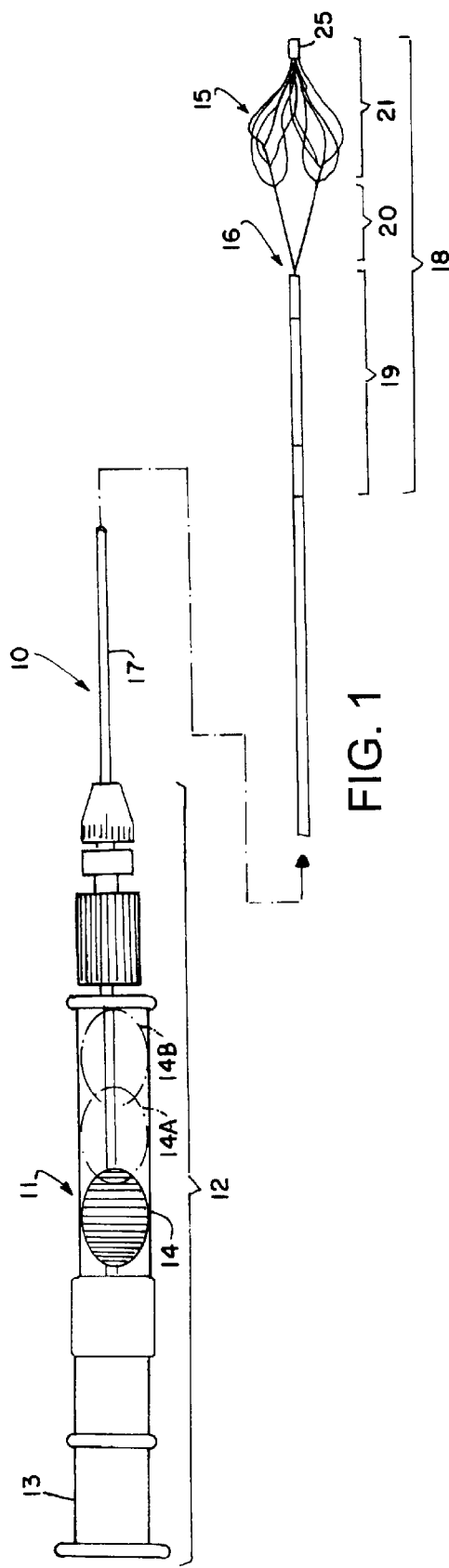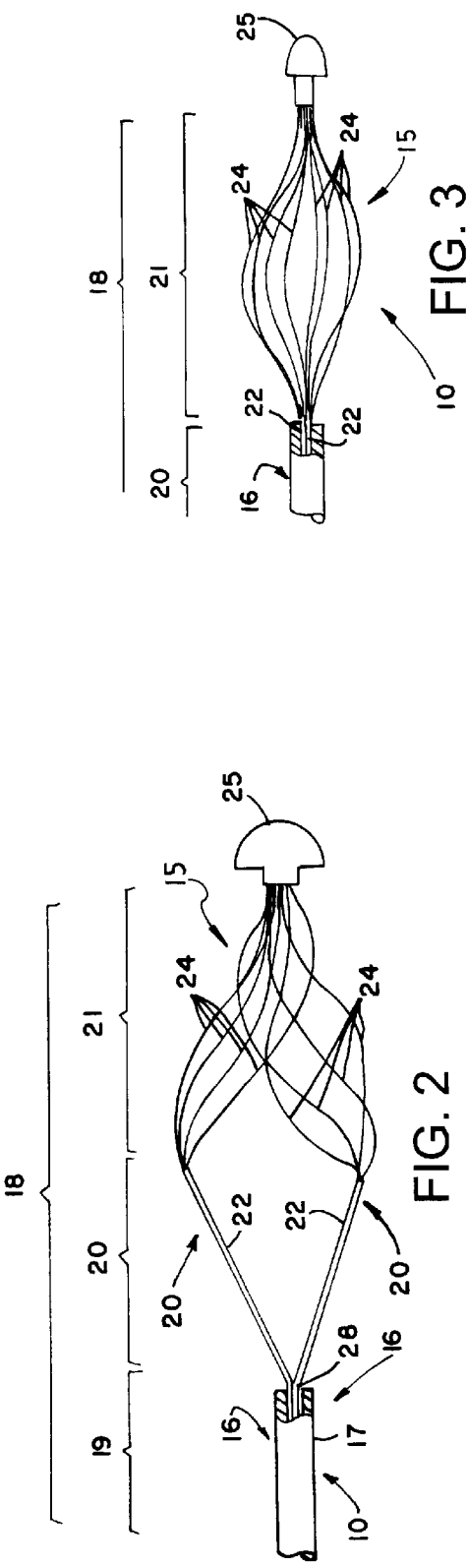

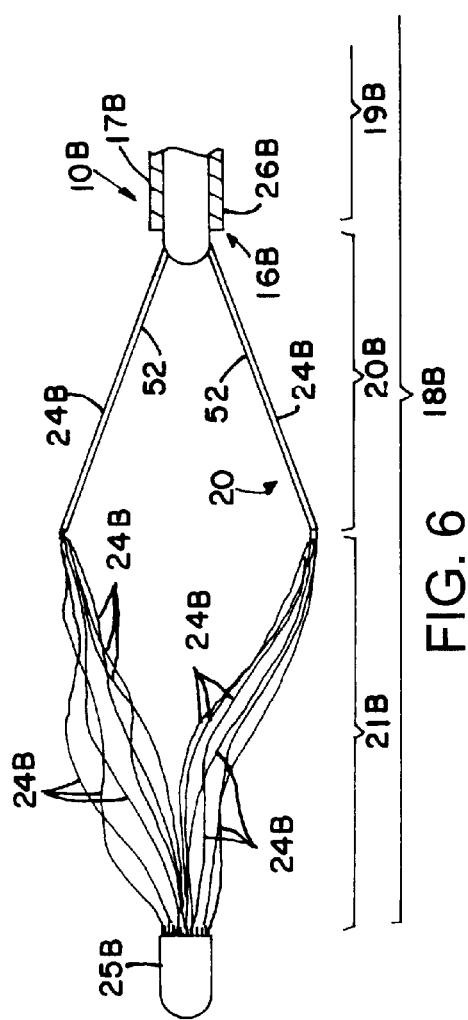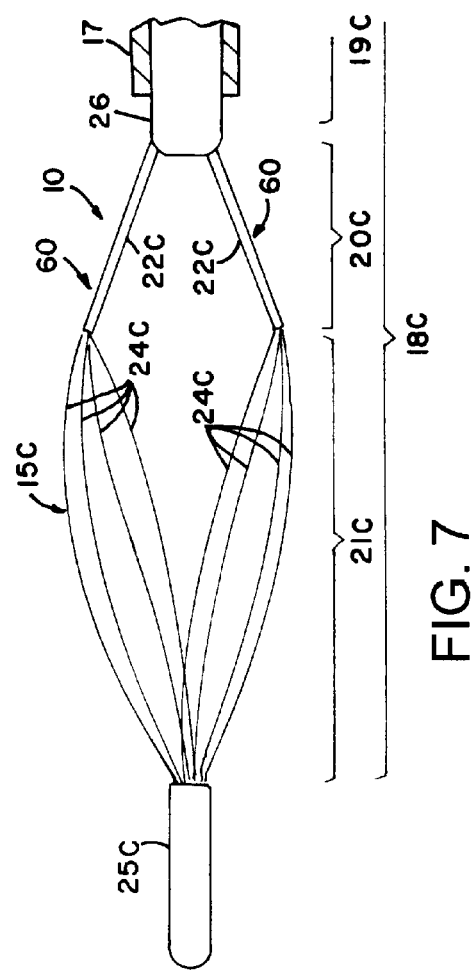

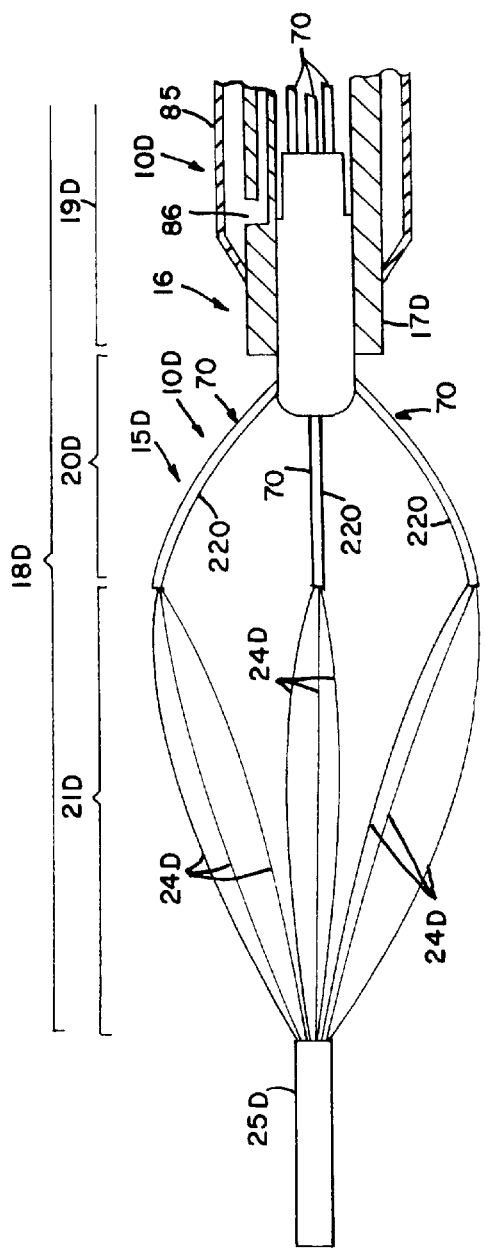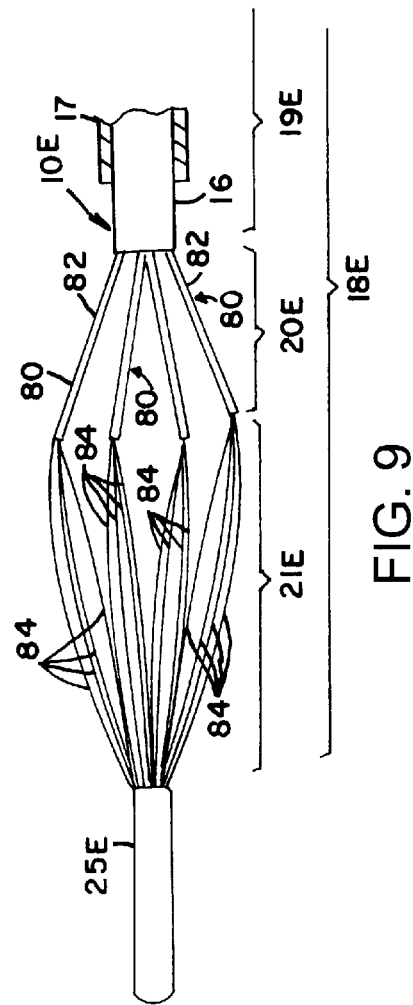
FIG. 8
FIG. 9

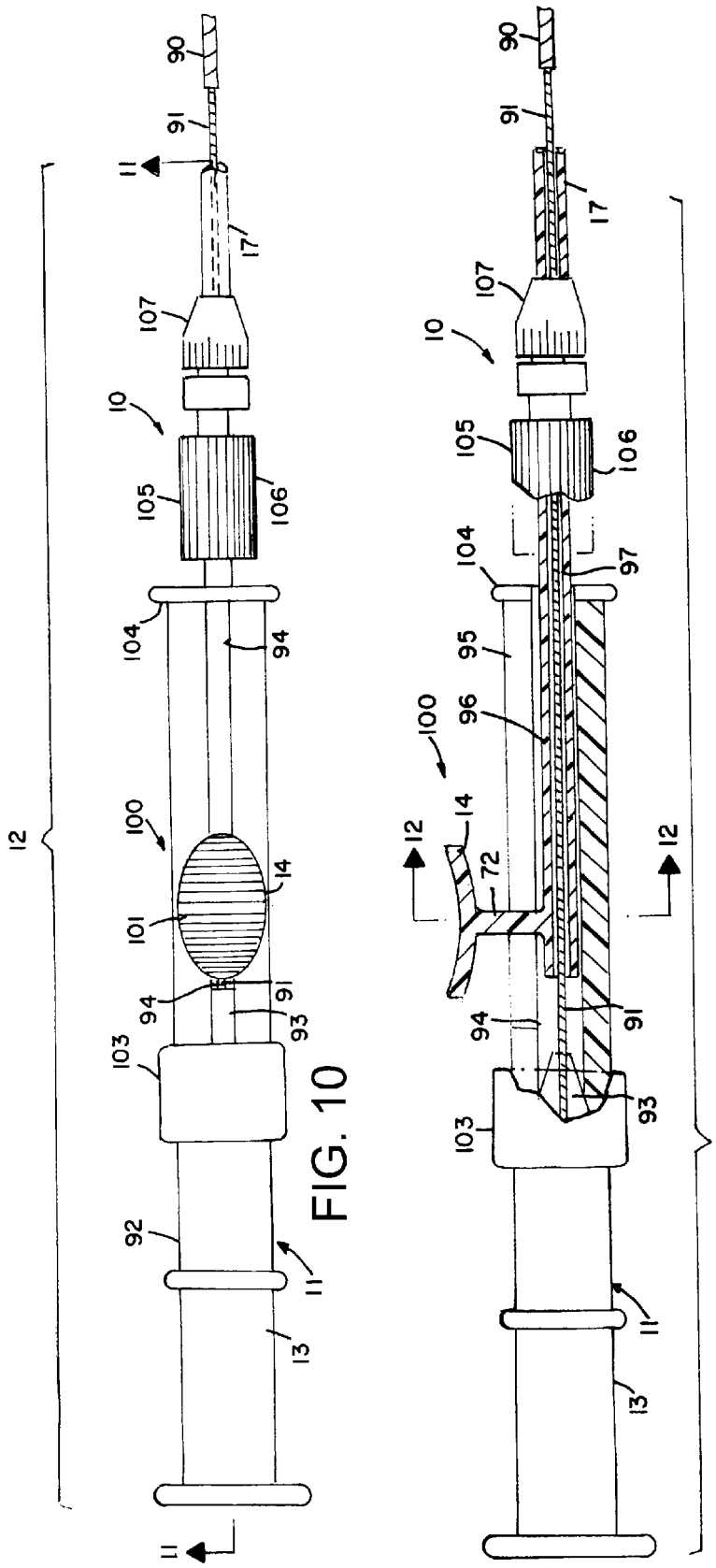

SURGICAL EXTRACTOR

This is a continuation of U.S. patent application Ser. No. 09/636,213 file Aug. 10, 2000, now U.S. Pat. No. 6,383,196 allowed, which is a continuation of U.S. patent application Ser. No. 08/968,906, filed Nov. 6, 1997 and issued as U.S. Pat. No. 6,168,603, which is a continuation of U.S. patent application Ser. No. 08/822,207, filed Mar. 20, 1997, abandoned, which is a continuation of U.S. patent application Ser. No. 08/382,778, filed Feb. 2, 1995, abandoned.

BACKGROUND OF THE INVENTION

1. Field of the Invention

This invention generally relates to medical instruments and more specifically to an extractor for removing an object from a body, particularly calculi that can form in the biliary and urinary systems.

2. Description of Related Art

Recently developed medical instruments reduce the invasiveness and potential trauma previously associated with various medical procedures. The removal of calculi in the form of kidney stones, gallstones and the like from the body is one area where this effort is meeting with success. Various instruments now permit the removal of kidney stones and gallstones without the need for major surgery. Some of these instruments incorporate miniaturized grasping forceps. This invention, however, is directed to an alternative set of instruments that utilize mechanical retrieval baskets.

The following United States Letters Patents and United States Patent Application describe various types of such retrieval baskets:

U.S. Pat. No. 4,346,846 (1982) Dormia
U.S. Pat. No. 4,590,938 (1986) Segura et al.
U.S. Pat. No. 4,611,594 (1986) Grayhack et al.
U.S. Pat. No. 4,625,726 (1986) Duthoy
U.S. Pat. No. 4,807,626 (1989) McGirr
U.S. Pat. No. 5,064,428 (1991) Cope et al.
Ser. No. 08/258,121 (1994) Bates et al.

Dormia discloses a retrieval basket at a distal end of a surgical extractor selectively extended beyond a tube in an enlarged condition. The retrieval basket comprises a plurality of wire pairs with the wires in the pairs extending in opposite helical wound paths to provide relatively closer wire spacings in the distal end of the enlarged retrieval basket compared to the proximal end. The differential wire spacing promotes the capture of objects in the middle portion of the retrieval basket and entrapment of such objects in the distal end of the retrieval basket.

Segura et al. disclose a medical retrieval device that can be inserted through the working channel of an endoscope for removing stones and the like from the kidneys or the ureter or biliary duct. A retrieval basket of relatively large diameter extends from the distal end of a sheath and collapses into a compact form when drawn into the sheath. Individual outwardly bowed spring strips form the retrieval basket. These strips extend generally axially of the sheath and join at respective distal and proximal ends. The retrieval basket has a generally bulbous form which is relatively stiff due to the spring strip construction and facilitates dislodgment and capture of stones.

The Grayhack et al. patent discloses another retrieval basket that is useful during the removal and/or destruction of calculi. A smooth outer tubular sheath overlies and contains a stranded wire cable terminating in a protective tip at the working or distal end of the device. When the cable is extended distally, the individual spring wire strands at the working end of the cable expand to form a retrieval basket. The distal end of this device additionally includes an expandable distal portion for protecting surrounding tissue during withdrawal of the device and calculi.

The Duthoy patent discloses an extraction device that includes a retrieval basket formed from a plurality of individual wires spaced about and outwardly from an imaginary extension of the center line of a hollow cable. A filiform extends distally from the distal end of the retrieval basket to extend past a stone and to allow the basket to be threaded around and onto the calculi.

The McGirr patent discloses an extractor including a self-closing retrieval basket at the distal end of a catheter with a flexible control line for opening the retrieval basket from the proximal end of the catheter. The retrieval basket assumes a normal position wherein it is in a compact closed form. Pulling on the control line flexes individual strips which define the retrieval basket to open the retrieval basket. When the control line is released, the strips relax and surround the calculi or object being removed.

Cope et al. disclose a stone retrieval basket having superelastic individual wire loops secured together at the apex of the loops to define a distal end of a retrieval basket which can be insert through and beyond a distal end of an elongated tube. Sleeves which secure the wires in a spaced relation and defines the proximal end of the retrieval basket, so the retrieval basket has a bulbous shape.

Bates et al. disclose, in a co-pending patent application commonly assigned with this application, a surgical retrieval basket comprising axially extending wires that are grouped in sets of filaments. The wires are normally maintained in an overlying sheath in a compact condition and form an enlarged retrieval basket upon retraction of the sheath. The individual filaments in a set are relatively closely angularly spaced with the sets being relatively widely spaced to provide a greater number of contact points with entrapped calculi without significantly increasing the manipulations necessary to capture such calculi in the retrieval basket.

These and other surgical extractors using retrieval baskets have certain common characteristics. Each retrieval basket comprises a plurality of filaments in the form of individual strands, strips or wires that extend from a proximal end of the retrieval basket to the distal end of the retrieval basket and, as disclosed by Cope et al., back to the proximal end. In some retrieval baskets the strands are formed along substantially straight lines when the retrieval basket is in a compact form; in others, along a generally helical path. Each instrument includes a plurality of three or more such individual strands to provide contact points for entrapping objects and between which the objects must pass for capture within the retrieval basket.

Retrieval baskets preferably include sufficient numbers of closely spaced wires to provide an enclosure for retaining objects captured within such retrieval baskets while having relatively few widely spaced wires for promotion of capture of such objects. Additionally, the overall size or diameter of an extractor and ancillary equipment, such as an endoscopic device, can impose upper limits on the number of wires and the size of the individual wires. Thus, the design of such baskets involves a compromise between the numbers of wires needed to retain objects and to promote capture of such objects and the overall size of such wires for sufficient strength of the basket.

The following United States Letters Patents and United States Patent Application describe retrieval baskets that include a material coating over the distal end of the baskets to encapsulate objects to be removed from the body:

U.S. Pat. No. 3,472,230 (1969) Fogarty

U.S. Pat. No. 4,790,812 (1988) Hawkins, Jr. et al.

Fogarty discloses a surgical retrieval basket that extends from the distal end of a catheter and comprises four spring wires that to a slide. An umbrella of suitable flexible material is connected to the distal portion of the wires so that upon deployment of the retrieval basket the edges of the umbrella form a circular scrapper. Retracting the retrieval basket from a deployed condition toward and then into a proximal sheath removes debris from a body passage with the umbrella retaining and then closing upon the captured debris.

Hawkins, Jr. et al. disclose a parachute retrieval basket deployed from the end of a catheter. The retrieval basket comprises four individual helically wound spring wires that extend between proximal to distal ends of the basket. A thin, porous fabric web secures and covers the distal portion of the wires to thereby prevent passage of debris, such as emboli or atheroma therethrough.

These and other surgical extractors having a unitary material web at the distal end have certain common characteristics. Each retrieval basket comprises a plurality of filaments in the form of individual strands, strips or wires that extend from a proximal end to the distal end of the retrieval basket. Like the previously described retrieval baskets, the strands lie either along substantially straight lines or extend along a generally helical path when the retrieval basket is in a compact form. The retrieval baskets include at least four individual strands to which the web is attached along a distal portion.

The design of a web retrieval basket is also a compromise between (1) the numbers of the strands necessary to deploy the web in a sufficiently open, radially-extended edge, (2) the numbers of wires to promote passage of objects through the wires into the retrieval basket, and (3) the overall size or diameter of an extractor and ancillary equipment, such as an endoscopic device with which the retrieval basket is used. These web baskets, however, are more difficult to manufacture than wire retrieval baskets, and further limit the diameter of the wires due to the space occupied by the web in the compacted condition.

Thus, additional wires in either a wire or web retrieval basket would be advantageous in certain respects and detrimental in others. For example, increasing the number of wires increases the number of contacts between the basket and any entrapped calculi and, in the case of a web basket more evenly opens the parachute. However, the resulting decrease in the spacing between such wires complicates the manipulations necessary for an expanded retrieval basket of either type to capture the calculi. Likewise, reducing the numbers of wires facilitates the capture of the object between the wires and selective release of the object, if needed. However, the fewer contact points between the captured object and the retrieval basket make retention and entrapment of such objects more difficult and, in the web basket, limit the radial extent of the web.

Additionally, most of these devices do not permit the retrieval basket to be dragged proximally along a surface to engage objects therealong. This would be particularly useful in the case of impacted calculi, e.g., kidney stones, that now frequently require major surgery due to the inability of the prior art devices to remove them. Thus, while the devices described above have some of the desirable features, none provide a device that is relatively simple to manufacture, promotes ease of capture of objects, promotes ease of percutaneous release of such objects, and promotes retention of relatively small objects captured.

SUMMARY

Therefore it is an object of this invention to provide a surgical extractor that increases the reliability of retaining entrapped objects in a retrieval basket.

Another object of this invention is to provide a surgical extractor that increases the number of contact points with entrapped objects in a distal portion of a retrieval basket without increasing the overall size of the instrument.

Still another object of this invention is to provide a surgical extractor that promotes the selective release of entrapped objects.

Another object of this invention is to provide a surgical extractor that enables the entrapment of objects embedded in bodily tissue.

Still another object of this invention is to provide a surgical extractor that increases the number of contacts with entrapped calculi in an extractor that is readily manufactured.

Still yet another object of this invention is to provide a surgical extractor that increases the number of contact points with entrapped calculi and promotes ease of capture of such calculi.

Still a further object of this invention is to provide a surgical extractor that provides an open wire web of a plurality of filaments in a distal portion and individual strands in a proximal portion to optimize both the entry and capture of objects in the proximal portion of the retrieval basket and retention of such objects in the distal portion of the retrieval basket.

Yet a further object of this invention is to provide a surgical extractor that provides relatively few individual wire strands to promote capture of objects.

Yet still a further object of this invention is to provide a surgical extractor that decreases the number of interfering contact point wires with an object at the proximal portion of the extractor while maximally increasing the number of contacts with the object at a distal portion to retain such object.

In accordance with this invention a surgical extractor for removing an object from a body includes a retrieval basket with distal and proximal ends and a retractable sheath. The retractable sheath in a first position retains the retrieval basket in a compact condition and in a second position frees the retrieval basket for expansion to form an enlarged basket that comprises a plurality of wires extending between the distal and proximal ends of the basket. Each of the wires of the basket comprises a first section having an individual strand extending from one end, such as the proximal end, of the basket and a second section having a plurality of individual filaments that extend between the other end, such as the distal end, of the basket and the strand.

According to another aspect of this invention a surgical extractor for removing an object from a body comprises a handle extending along an axis that includes a base for being grasped by a physician and a slider for axial reciprocation relative to the base. The base connects with basket forming means for forming a enlarged basket distally of the handle. The basket includes a set of spaced, spring formed wires with each of the wires have a first section comprising an individual strand and a second section comprising a plurality of spaced filaments of wires. A sheath connects to the slider for axial displacement with respect to the basket whereby the sheath in a first position retains the wires and in a second position exposes the first and second sections of the wires to enable the wires to expand and form the basket.

According to a further aspect of this invention a surgical extractor for removing objects from a body comprises an axially extending, molded plastic, partially hollowed base and a support. The support includes a solid stainless steel, radially flexible, axially stiff rod attached to and extending distally from the base, a stainless steel cable extending distally from the rod and a connector axially connecting the rod and cable. A plurality of spaced stainless steel wires attached to the distal end of said cable. Each wire has a proximal portion comprising an individual strand and a distal portion comprising a plurality of filaments. Proximal movement of a plastic slider captured in the base moves a polyimide sheath and exposes the wires whereby the sheath compacts and retains said wires at substantially a given diameter in its distal position and releases the wires from their compact form to thereby form an enlarged retrieval basket.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

FIG. 1 is a plan view of a surgical extractor constructed in accordance with this invention with a handle at a proximal end and an expanded retrieval basket at a distal end;

FIG. 2 is a enlarged view, partially in cross section, of the distal end of the extractor of FIG. 1;

FIG. 3 is a enlarged plan view of the distal end of the extractor of FIG. 1 with the retrieval basket in a reduced, expanded form;

FIG. 6 is an enlarged plan view similar to FIG. 5 of still another embodiment of a retrieval basket in an expanded form;

FIG. 7 is an enlarged plan view similar to FIG. 5 of yet another embodiment of a retrieval basket in an expanded form;

FIG. 8 is an enlarged plan view similar to FIG. 5 of yet still another embodiment of a retrieval basket in an expanded form;

FIG. 9 is an enlarged plan view similar to FIG. 5 of a further embodiment of a retrieval basket in an expanded form;

FIG. 10 is an enlarged plan view of the handle at the proximal end of the extractor shown in FIG. 1;

FIG. 11 is another view, partially in section, taken along lines 11—11 in FIG. 10; and FIG. 12 is a cross sectional view taken along lines 12—12 in FIG. 11.

DESCRIPTION OF ILLUSTRATIVE EMBODIMENTS

Figure 4:
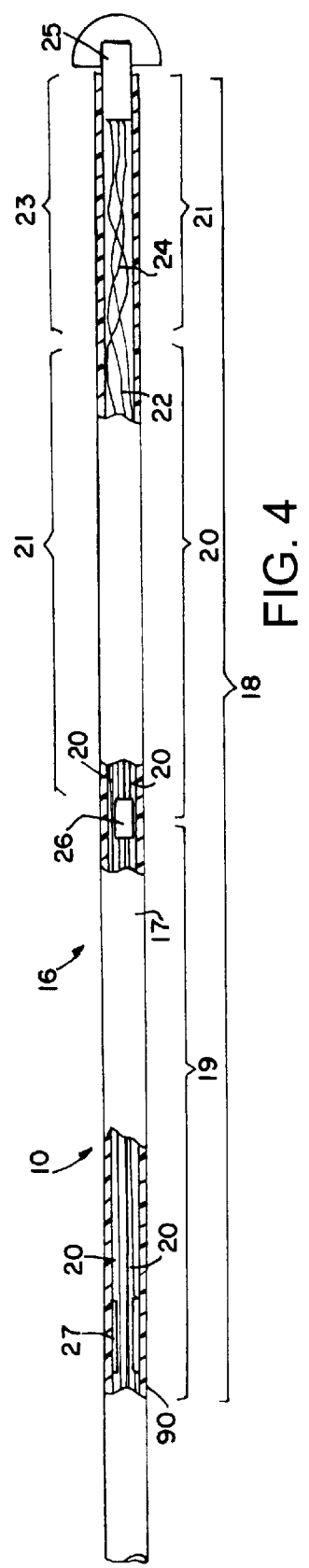
FIG. 4 is an enlarged view, partially in cross section, of the distal end of the extractor shown in FIG. 1 with the retrieval basket in a compact form.

FIG. 1 depicts one embodiment of a surgical extractor 10 constructed in accordance with this invention. The surgical extractor 10 includes a handle 11 at a proximal end 12 having a base 13 and a slider 14. A physician can grasp the base 13 in the palm in his or her hand and manipulate the slider 14 with his or her thumb. A retrieval basket 15 formed in accordance with this invention is located at the distal end 16 of the extractor 10. A sheath 17 overlies an intermediate supporting structure between the handle 1 and the retrieval basket 15.

As shown in FIG. 1 the slider 14 is located at a proximal position 14A. As the slider 14 advances to a distal position 14B as depicted in phantom, the sheath 17 advances from the position depicted in FIG. 2 through the position shown in FIG. 3 to the position illustrated in FIG. 4. In FIG. 4 the sheath 17 compacts and covers the retrieval basket 15 within a central aperture of the sheath. The sheath 17 typically comprises a polyimide tube or a tube of another material that exhibits the radial flexibility, axial stiffness, biocompatibility and hoop strength of a polyimide tube.

FIG. 2 depicts the distal end 16 of the surgical extractor 10 in an enlarged form in which the retrieval basket 15 forms a basket assembly 18 comprising three axially extending sections 19, 20, and 21. The first, or most proximal, section 19 and the second, or intermediate, section 20 comprise individual prestressed strands 22. The third, or most distal, section 21 comprises prestressed filaments 24 that extend distally from each of the ends of the strands 22 to a cap 25.

Each of the strands 22 and the filaments 24 are formed of stainless steel or some other shape memory material. The cap 25 captures distal ends of all the filaments 24 by soldering the filaments 24 in the cap 25, by swaging or by some other method to define a distal end of the basket 15. A sleeve 26 defines the boundary of the first and second sections 19 and 20 and secures the strands 22 together thereat. The strands 22 lie in a parallel relationship between the sleeve 26 and a sleeve 27 located at the proximal end of the basket assembly 18. The individual strands 22 are prestressed or preformed so that without restraint they diverge from each other as they extend distally from the sleeve 26 through the intermediate section 20. The filaments 24 are preformed to follow a helical path from the ends of the strands 22 to converge at the cap 25 to thereby define the third or most distal section 21 of the basket assembly 18.

While FIG. 4 illustrates the strands 22 extending essentially parallel to each other in the first and section 19, it will be understood that the strands 22 could be intertwined or twisted while still retaining a compact cross-section. Additionally, the strands 22 in the second section 20 could be preformed or stressed to follow a helical path between the sleeve 26 and the third section 23. With either of these constructions, the distal end 16 of the extractor 10 remains radially flexible and, by virtue of the sheath 17, axially stiff to facilitate placement of the extractor 10. The combination of radial flexibility and axial stiffness is particularly important when the extractor 10 has the form shown in FIG. 4 with the sheath 17 advanced distally to the cap 25.

More specifically, a physician will introduce the extractor 10 with its distal end 16 in the form shown in FIG. 4 so the sheath 17 retains the retrieval basket 15 in its compact form. When the distal end 16 is positioned proximate at calculi or any other object to be retrieved, the physician moves the slider 14 from position 14B to the position 14A in FIG. 1. This retracts the sheath 17 and exposes the second and third sections 20 and 21 of the basket assembly 18. The wires return to their original shape as shown in FIG. 2 thereby to dilate surrounding tissue and to provide a structure that can be manipulated to capture calculi within the confines of the retrieval basket 15. Preferably, the distal end 16 of the extractor 10 is positioned distally of the object prior to displacement of the sheath 17 so that the intermediate section 20 is adjacent or distally proximate the object to ease and speed capture of the object within the basket.

With the present invention, a physician can manipulate the retrieval basket 15 so that the calculi or other objects between the filaments 24 or strands 22 in much a similar manner as in prior art retrieval baskets. However, the reduced number of strands 22 in the intermediate section 20 greatly eases and simplifies this task.

Two different procedures for capturing calculi and the like demonstrate the ease with which the task can be realized. In a first, the physician positions the distal end 16 of the extractor 10 to or beyond the calculi, moves the retrieval basket 15 out of the sheath 17 so the retrieval basket 15 expands beyond the calculi. As the physician displaces the retrieval basket 15 proximally, the strands 22 can straddle the calculi and allow the filaments 24 to capture the calculi. As an alternative, the distal end 16 can be positioned so the compacted retrieval basket 15 is coextensive with the calculi. Retracting the sheath 17 enables the retrieval basket 15 to expand around the calculi so subsequent withdrawal enables the strands 24 to capture the calculi.

The increased number of filaments 24 in the distal section 21 that engage the calculi and urge it along as the extractor moves proximally reduces the chances that the calculi can move between adjacent filaments. The close spacing of the filaments 24 also allows for entrapment and retention of small objects which would not ordinarily be retained in retrieval baskets having the relatively wide spacing of the strands 22 necessary to capture larger objects. Moreover, this feature can be particularly useful in removing impacted or embedded calculi that in the past generally required major surgery for removal, as the retraction of the basket 15 over such calculi tends to scoop it into the third, web-like section 21.

Once the physician has moved calculi into the distal portion 10 of the retrieval basket 15, the physician advances the sheath 17 distally and reduces the volume of the retrieval basket 15 until it contacts the entrapped calculi (e.g., the volume of the basket shown in FIG. 3 with the slider 14 in the position 14C shown in phantom in FIG. 1). Then the physician withdraws the extractor 10 with the entrapped calculi from the patient.

In some situations during withdrawal of the extractor 10, the retrieval basket 15 and entrapped calculi must pass a stricture in a vessel. In such situations it may be desirable to terminate the procedure and withdraw the extractor 10. With the extractor 10 according to this invention, the physician positions the distal end 16 distally of the stricture in a relatively open portion of the vessel. The physician then manipulates the retrieval basket 15 to urge the calculi to the proximal end of the expanded basket (i.e., the intermediate section 19) where the strands 22 are widely spaced relative to the filaments 24 and the calculi are most readily released from the retrieval basket 15. Then the physician can advance the sheath to retain the retrieval basket 15 in its compact form thereby to facilitate the removal of the extractor 10 from the body of the patient.

During manufacture of the specific embodiment of FIGS. 1 through 4, composite wires 28 are formed to extend axially with the strand 22 constituting a first axial portion from which the second comprising the four individual filaments 24 extends. The distal ends of all the filaments 24 are soldered or swaged into the cap 25. The sleeve 26 engages the strands 22 at the juncture of the first and second axial sections 19 and 20. It will be understood that the strands 22 can comprise extensions of the four individual filaments 24 that are secured or otherwise entwined. Alternatively, the filaments 24 can constitute separate filaments that attach to the distal end of each of the strands 22 that comprise solid or braided wire. Applicants also note as a further alternative that the sets of threads such as those disclosed by the Bates et al. in U.S. patent application Ser. No. 08/258,121 and incorporated by reference herein can also be used with the present invention. Specifically, each of the strands 22 forming the proximal portion 18 of the retrieval basket 15 of FIG. 2, for example, would comprise a plurality of closely spaced filaments and/or each of the filaments 24 in the distal portion 19 of the basket 15 would comprise a plurality of closely space threads. In essence, this invention allows the construction of a retrieval basket in which the form and materials of the first and second sections 20 and 21 can be tailored to meet criteria including strength and flexibility.

After forming the composite wires 28 and attaching the cap 25 and the sleeve 26, prestressing the wires 28 occurs to form the retrieval basket 15. The wires 28 intermediate the cap 25 and the sleeve 26 in the opposed ends of a forming tool. This tool extends transversely from a center axis by a distance corresponding to the desired diameter of the retrieval basket 15. It rotates about its axis in the plane of the wires back and forth approximately +75° and 75° so that each end of the tool slides along one of the wires and urge, and thus prestress, both of such wires radially outward to define the basket 15 with the desired diameter.

After the first tool is removed, two circular forming tools receive a distal and proximal portion, respectively, of each of the filaments 24 with the filaments disposed essentially equiangularly about the tools. Rotation of the tools in opposite directions (i.e., counter-clockwise and clockwise directions) prestresses the filaments 24 in the helical fashion illustrated in FIGS. 1, 2 and 3. Consequently, the two strands 22 are equiangularly spaced apart to facilitate the capture of large objects within the basket 15 while the relatively close angularly spacing, approximately 45°, of the filaments improves retention of smaller objects in the web-like, distal portion of the basket 15. It should also be understood that the filaments 24 may be preformed similarly to that described above with respect to the strands 22 (i.e., straight wire), and the strands 22 also may be preformed in the same manner as the filaments 24 (i.e., helically wound).

Retrieval baskets according to this invention enable a user to select a retrieval basket which has both the advantages of baskets with a relatively few widely equiangularly spaced wires and those with closely spaced wires, while avoiding the disadvantages associated with each. That is, the use of multiple filaments 24 in the third, or most distal section 21 increases the number of contact points with any entrapped calculi whereas the more widely spaced strands 24 in the intermediate section 20 promote capture of such calculi. In FIG. 2, for example, the eight filaments 24 of the wires 28 provide multiple contacts for calculi therein rather than the contact which would be provided with a pair of the individual strands 22 extended through the third, or most distal, section 21. The close equiangular spacing of the filaments 24 also permits the retrieval basket 15 to accommodate surface unevenness of such calculi to thereby increase its reliability and suitability. The reduced number of strands 22 within the intermediate section 20 and increased angular spacing between adjacent ones of the strands 22 allow a physician to maneuver the basket 15 to entrap and retain calculi more easily. This increased facility by means of increased numbers of filaments, such as quadrupling from two strands 22 to eight filaments 24, occurs without increasing the overall size of the sheath 17 and without reducing the strength of the retrieval basket 15. For example, it is possible to place two individual strands having a diameter of 0.010" in a sheath 17 with an outside diameter of 3.0 Fr and to place eight filaments having a diameter of 0.006" in the same sheath due to the change in packing efficiency.

When the sheath 17 moves from the position shown in FIG. 4 to the position shown in FIG. 3, the expanded portion of the retrieval basket 15 comprises only the distal section 21 of the basket 15. This configuration of the basket, while not providing the physician with the same overall size and consequently narrow angular spacing of the filaments through which the calculi must pass, can be used in locations where full expansion of the basket is impractical such as close to the wall of an organ or a narrow or otherwise weakened lumen in the body. In any event, this feature allows further and diverse use of the retrieval basket of this invention compared to prior retrieval baskets.

Figure 5:
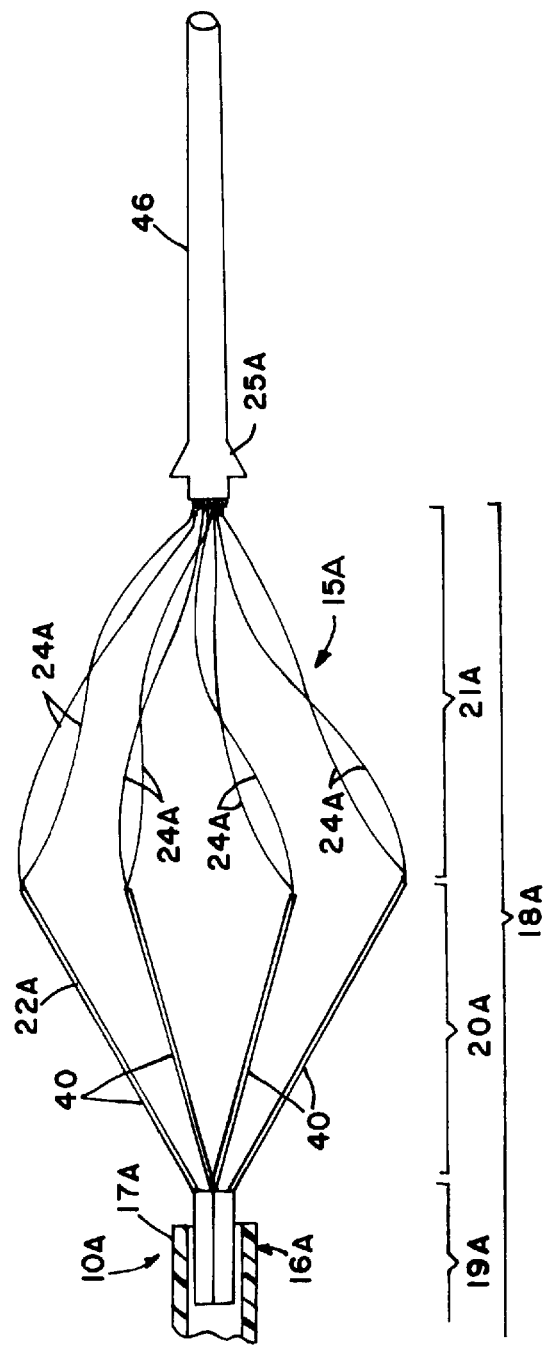
FIG. 5 is an enlarged plan view of the distal end of another surgical extractor incorporating another embodiment of a retrieval basket in an expanded form.

FIG. 5 depicts an alternative embodiment of a retrieval basket 15A and sheath 17A at a distal end 16A of the extractor 10A. In this particular embodiment, the retrieval basket 15A comprises four wires 48. Each of the wires 48 comprises a first section 48A and a second section 48B. The first section 48A of each of the wires 48 comprises an individual strand 22A extends through first and second sections 19A and 20A of a basket assembly 18A. The second section 48B of each of the wires comprises two filaments 24A extending from the distal end of the associated one of the individual strands 22A to a cap 25A to define a third distal section of the basket assembly 18A. The cap 25A captures the ends of all the filaments 24A to define the distal end of the basket 15A, and a sleeve connector 26A that secures the strands 22A together defines the proximal end of the basket 15A. In this particular embodiment each of the strands 22A are angularly spaced by about 90° from adjacent strands, while the filaments 24A are helical wound and angularly spaced by about 45°. In this particular embodiment, a filiform 49 extends distally from the cap 25A. Such filiforms are know in the art and can be included as an element in any embodiment of this invention.

FIG. 6 depicts only second and third sections 20B and 21B of the basket assembly 18B at the distal end 16B of another embodiment of a surgical extractor 10B. Retraction of a sheath 17B at the distal end 16B of the surgical extractor 10B to the illustrated position enables the second and third sections 20B and 21B to form the enlarged retrieval basket 15B extending between a cap 25B and a sleeve 26B. Two wires 58 define the retrieval basket 15B, with each of the wires comprising a individual strand 22B extending distally from the proximal end of the end of the basket and six filaments 24B extending proximally from the distal end of the basket to the distal end of the associated strand 22B. The filaments 24B in this instance are prestressed to follow a helical path. The strands 22B of this embodiment comprise the associated filaments 24B secured together. Specifically, the filaments 24B are secured together by being entwined to define each of the strands 22B.

FIGS. 7, 8 and 9 illustrate other surgical extractor embodiments constructed in accordance with this invention. The retrieval baskets 15C, 15D, and 15E of the extractors 10C, 10D and 10E comprise a plurality of wires with each of the wires having substantially more filaments in the distal portion of the basket than strands in the proximal portion. For example, each of the two wires 68 of the basket 15C of FIG. 7 comprises a strand 22C in the proximal section 21C and five filaments 24C in the distal section, while each of the three wires 78 of the basket 15D of FIG. 8 comprise a strand 22D and three filaments 24D. Four wires 80 define the basket 15E of FIG. 9. Each includes an individual strand 22E and four filaments 24E. Although, each of the filaments 64, 74, and 84 of the baskets 15C, 15D, and 15E are prestressed, they are not helically wound like the filaments of the baskets 15, 15A and 15B of FIGS. 1 through 6. That is each of the filaments 24E between one of the strands 82 and the cap 25E is prestressed to extend radially away from the axis of the basket 15E and to be spaced from each of the other filaments. It will also be noted that the extractor 10D of FIG. 8 also includes an expansible balloon 85 connecting through a port 86 within an inflation source (not shown) for selective inflation of the balloon 85.

The baskets 15, 15A, 15B, 15C, 15D, and 15E described in connection with FIGS. 1 through 9 may also be formed by the method described in the co-pending, commonly assigned U.S. patent application Ser. No. 08/342,911 filed on Nov. 21, 1994, "SURGICAL RETRIEVAL BASKET AND METHOD FOR MAKING THE SAME". Using the process described therein provides strands and filaments with improved strength, durability and other characteristics.

As previously indicated with respect to FIG. 1, the sheath 17 extends between the handle 11 and the distal end 16. An interconnecting link allows the slider 14 to move the sheath 17 relative to the distal end 16. This link comprises a radially flexible, axially stiff stainless steel cable 90 that is shown at its distal end in FIG. 4, and at its proximal end in FIGS. 7 and 8. The sheath 17 retains the cable 90 on its axis.

Now referring to FIGS. 7 through 9, the proximal end of the cable 90 attaches to a rod 91 by swaging, soldering or other method. The rod 91 extends proximally into the handle 11. More specifically, the handle base 13 includes a hollowed handle portion 92 with an internal boss or receptacle 93 that receives the proximal end of the rod 91. Typically the proximal end of the rod 91 will be affixed in the receptacle 93 by an adhesive, ultrasonic or other fastening technique. Consequently, the rod 69, the cable 90 and the basket 15 are fixed spatially with respect to the handle 11.

The slider 14 rides in an axially extending chamber 94 within the base 13 formed with a radially extending slot 95. The slider 14 comprises a cylindrical, elongated body 96 that has a radial passageway 97 for allowing the cylindrical body 96 to slide axially and freely in the chamber 94 with respect to the base 13 and the rod 91.

A thumb actuator 100 includes a thumb pad 101 and radial arm 102 that are molded integrally with and extend radially from the cylindrical body 96. The arm 102 extends through the slot 95 and is therefore slidable along the axis of the extractor 10 between distal and proximal positions. In this particular embodiment the base portion 11 includes radially extending bosses 103 and 104 that define the proximal and distal terminations of the slot 95 respectively. The slider than moves between a proximal position, defined when the arm 102 reaches the boss 103, and a distal position defined when the arm 102 reaches the boss 104.

The distal end of the cylindrical body 96 supports a. Luer-lock fitting 105. A first component or base 106 attaches to the cylindrical body 96 and includes an axially extending aperture that allows the rod 91 to pass through the fitting 105. A detachable component 107 carries the sheath 17. Consequently, as a physician moves the thumb actuator pad 101 between proximal and distal positions, the slider 14 and the sheath 17 move relative to the rod 91, the cable 90 and the retrieval basked 15 (FIG. 1). Further as the thumb pad 101 moves toward the distal position, the distal end of the sheath 17, as shown in FIGS. 2 and 3, advances over and compacts the strands 22 of the retrieval basket 15 due to the axial stiffness and hoop strength of a polyimide tube or tube of similar material.

Therefore, in each of the specifically disclosed embodiments an extractor that meets the various objects of this invention. The extractor simplifies the capture and release of objects by providing a relatively few wires comprising individual strands at the proximal end of the basket. The extractor also provides for improved retention of objects captured thereby by providing a basket with a plurality of wires with a plurality of filaments at the distal end. Specifically, in each embodiment spaced, preformed wires each have individual strands in the proximal section and a plurality of spaced filaments at the distal portion. The spaced filaments increase the number of contact points with an entrapped calculi at the distal section of the basket. Yet there is no concomitant increase in the contact points in the number of wires or strands in the proximal section of the basket.

This invention has been disclosed in terms of certain embodiments. It will be apparent that many modifications can be made to the disclosed apparatus without departing from the invention. For example, FIGS. 1 and 2 depict a retrieval basket 15 with two prestressed strands 22 and eight filaments 24. Each set of four filaments is interconnected only at the ends thereof. Consequently the filaments 24 in each set may be widely spaced where they join their respective strands 22. This opening, in appropriate circumstances, might be reduced by interconnecting adjacent strands from each set by a connector, by joining or by some other means. Therefore, it is the intent of the appended claims to cover all such variations and modifications as come within the true spirit and scope of this invention.

What is claimed as new and desired to be secured by Letters Patent of the United States is:

1. A method of manufacturing a surgical extractor, comprising:
    forming a plurality of wires, each wire comprising a strand and a plurality of filaments that extend from a distal end of the strand, wherein the strand has a first axial portion and a second axial portion, the second axial portion located intermediate to the first axial portion and the plurality of filaments;
    preforming at least one of the plurality of wires by stressing the second axial portion of the strand of the wire to diverge outward to define a basket having a desired diameter; and
    assembling the surgical extractor from the plurality of wires.

2. The method of claim 1, wherein preforming comprises preforming a pair of the plurality of wires by stressing the second axial portion of each strand of each wire of the pair of wires to diverge outward to define the basket having the desired diameter.

3. The method of claim 1, further comprising capping together a distal end of each one of the plurality of filaments of each one of the plurality of wires.

4. The method of claim 1, further comprising attaching a sleeve to the plurality of wires, the sleeve defining a boundary between the first axial portion and the second axial portion of each strand.

5. The method of claim 1, further comprising preforming the plurality of filaments of each of the plurality of wires in a helical fashion.

6. The method of claim 5, wherein preforming the plurality of filaments comprises rotating in opposite rotational directions distal and proximal portions of each of the plurality of filaments of each of the plurality of wires.

7. The method of claim 1, further comprising preforming the strands in a helical fashion.

8. The method of claim 1, wherein forming the plurality of wires comprises forming the plurality of wires at least in part from a shape memory material.

9. The method of claim 8, wherein the shape memory material comprises stainless steel.

10. The method of claim 1, further comprising soldering the distal ends of the filaments.

11. A method of removing an object from a body, comprising:
    providing an extractor comprising a retrieval basket with a distal end and a proximal end, a plurality of wires extending between the distal and proximal ends of the basket, each of the wires comprising an individual strand extending from the proximal end of the basket, a plurality of spaced filaments extending between the strand and the distal end of the basket, and a sheath comprising a lumen for retaining the strands and filaments of the retrieval basket in a first position in a compact condition within the sheath lumen, and for freeing the retrieval basket in a second position for expansion to form an enlarged basket for retrieving an object;
    positioning a distal end of the extractor adjacent to the object;
    moving the retrieval basket out of the sheath; and
    capturing the object by the plurality of filaments of the plurality of wires.

12. The method of claim 11, wherein positioning comprises positioning the retrieval basket in a compact condition coextensive with the object, and moving the retrieval basket comprises retracting the sheath to enable the retrieval basket to expand around the object.

13. The method of claim 11, wherein positioning comprises one of positioning the distal end of the extractor at and beyond the object, and moving the retrieval basket comprises causing the retrieval basket to expand beyond the object, and capturing comprises displacing the retrieval basket proximally to capture the object by the plurality of filaments of the plurality of wires.

14. The method of claim 13, further comprising moving the sheath distally to reduce a volume of the retrieval basket.

* * * * *